United States Patent [19]

Rayle

[11] Patent Number: 6,057,477

[45] Date of Patent: May 2, 2000

[54] METAL SALT CATALYZED PROCESS TO OXAZOLINES AND SUBSEQUENT FORMATION OF CHLOROKETONES

[75] Inventor: Heather Lynnette Rayle, North Wales, Pa.

[73] Assignee: Rohm and Haas Company, Phila., Pa.

[21] Appl. No.: 09/293,119

[22] Filed: Apr. 16, 1999

Related U.S. Application Data

[60] Provisional application No. 60/082,537, Apr. 21, 1998.

[51] Int. Cl.[7] .................... C07C 235/74; C07C 235/84
[52] U.S. Cl. ........................... 564/186; 564/215
[58] Field of Search ...................... 564/186, 215

[56] References Cited

U.S. PATENT DOCUMENTS

| | | |
|---|---|---|
| 4,822,902 | 4/1989 | Carley et al. . |
| 5,304,572 | 4/1994 | Michelotti et al. . |
| 5,922,916 | 7/1999 | Rayle et al. ............... 564/487 |

FOREIGN PATENT DOCUMENTS

WO 95/19351  7/1995  WIPO .

OTHER PUBLICATIONS

Transformations of the Herbicide N–(1, –dimethylpropynyl)–3,5–dichlorobenzamide in Soil, Roy Y. Yiu, et al., *Weed Science*, vol. 18, Iss. 5, pp. 604–607 (Sep. 1970).

Identification of Metabolites of N–(1, 1–Dimethylpropynyl)–3,5–dichlorobenzamide in Soil and Alfalfa, Roy Y. Yih, et al., *J. Agr. Food Chem.*, vol. 19, pp. 314–317 No. 2, (1971).

Acetylenic Amines, XII. Some New Reactions of Acylaminoacetylenes, Nelson R. Easton, et al., *J. Org. Chem.*, vol. 30, pp. 3084–3088 (1965).

*Primary Examiner*—Laura L. Stockton
*Attorney, Agent, or Firm*—Clark R. Carpenter

[57] ABSTRACT

This invention relates to a process for the preparation of an α-chloroketone compound comprising the steps of (i) cyclizing an alkynyl amide to form a 5-methyleneoxazoline

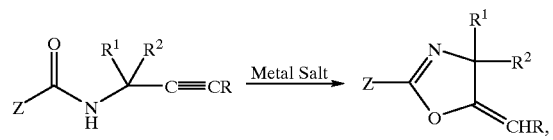

(ii) chlorinating the 5-methyleneoxazoline using trichlorolsocyanuric acid to produce a chlorinated oxazoline intermediate

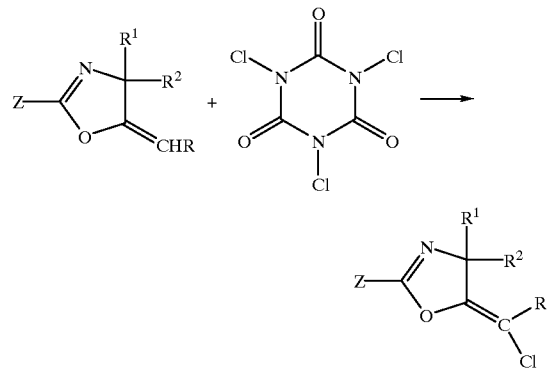

and (iii) hydrolyzing the chlorinated oxazoline intermediate with an aqueous acid to produce the desired monochloroketone

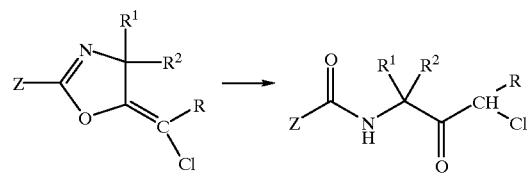

wherein Z is alkyl or substituted alkyl, aryl or substituted aryl, heteroaryl or substituted heteroaryl or phenylene, R is a hydrogen atom or alkyl, and $R^1$ and $R^2$ are each independently an alkyl or substituted alkyl group, or $R^1$ and $R^2$ together with the carbon atom to which they are attached form a cyclic structure. Additionally, when R is a hydrogen atom, a dichloroketone can be conveniently formed through adjustment of reaction conditions.

16 Claims, No Drawings

METAL SALT CATALYZED PROCESS TO OXAZOLINES AND SUBSEQUENT FORMATION OF CHLOROKETONES This application claims the benefit of U.S. Provisional Application Ser. No. 60/082,537 filed Apr. 21, 1998.

This invention relates to a novel, inexpensive process to prepare 5-methyleneoxazolines from substituted alkynyl amides. The 5-methyleneoxazoline is then converted to a 5-(chloromethylene)oxazoline using a convenient chlorinating agent followed by hydrolysis to an α-chloroketone. The 5-methyleneoxazoline has insecticidal properties and can be used as intermediates to herbicides and fungicides. The resulting α-chloroketones are useful themselves as fungicides.

There are several problems in the existing field which the present invention successfully overcomes. Previously disclosed routes to the desired 5-methyleneoxazoline from substituted alkynyl amides required the use of strong and, consequently, expensive bases such as sodium hydride or sodium amide. These bases require the use of scrupulously anhydrous conditions and are difficult to handle. Additionally, yields of the 5-methyleneoxazoline from the alkynyl amide are unacceptably low for economic viability. Other disclosed routes to the desired 5-methyleneoxazoline from substituted alkynyl amides involve treatment of the amide with a relatively large amount of a silver salt in N,N-dimethylformamide, a high-boiling, aprotic solvent. This type of procedure is expensive because of the amount of silver salt used and a solvent that requires a difficult work-up which produces large volumes of organic laden aqueous waste. Additionally, these procedures are intolerant to the presence of moisture; the presence of water in the solvent causes the formation of ketones in addition to or instead of the desired oxazoline. Still other disclosed routes employ water soluble solvents in a method to form a 5-methyleneoxazoline, but such solvents are difficult to efficiently recover and result in a process possessing undesirable cost.

The subsequent preparation of an α-chloroketone from the resulting 5-methyleneoxazoline by the known and usual methods, such as by using chlorine gas or N-chlorosuccinimide as the chlorinating agent, is also problematic because of a lack of selectivity for monochlorination; both underchlorinated and overchlorinated ketones are typically formed in addition to the desired monochloroketone after hydrolysis of the 5-chloromethylene oxazoline. Furthermore, the use of chlorine presents hazards and an equipment expense well known to those skilled in the art.

I have discovered a convenient process to 5-methyleneoxazolines from substituted alkynyl amides. A variety of solvents may be employed, and the presence of water is tolerated. Additionally, a much smaller amount of the metallic salt catalyst is employed than that disclosed previously. Furthermore, the complete process of this invention uses a novel chlorination reagent, trichloroisocyanuric acid (TCIA), which chlorinates the resulting 5-methyleneoxazoline selectively to give a monochlorinated intermediate which, upon acid-catalyzed hydrolysis, affords the desired α-monochloroketone selectively and in high yield. TCIA is a high melting, easily handleable solid which can be utilized in extremely precise amounts in order to avoid under- or over-chlorination of the desired material. Although TCIA is a well known, inexpensive and commercially available compound used in the chlorination of swimming pool water and the disinfection of drinking water, its use as a convenient and selective chlorination agent for 5-methyleneoxazolines had not been disclosed before this time. An additional feature of this invention provides a convenient process for the selective formation of α,α-dichloroketones which are also useful as fungicides.

WO 95/19351 discloses the formation of aryl-5-methyleneoxazole derivatives by cyclization of an alkynyl amide in the presence of a base. However, only the use of a large amount of strong base for the cyclization is exemplified. This procedure affords the oxazoline in low yield (<50%). The use of a strong base such as NaH requires anhydrous conditions. My invention is advantageous in that the presence of water is tolerated. Moreover, the use of a metal salt catalyst to facilitate the cyclization is not suggested.

Yih et al. in *Weed Science*, 18, 604–607 (1970) and in *J. Agr. Food Chem.*, 19, 314–317 (1971) disclose the formation of an aryl-5-methyleneoxazoline from a substituted alkynyl amide using acid, base or silver ion in an aqueous alcohol solution followed by hydrolysis to a ketone not possessing an α-chloro group. No experimental detail is provided in the 1970 paper; the 1971 paper provides a procedure whereby 28 mol % of silver nitrate in N,N-dimethylformamide solvent was employed. Easton et al. (J. Org. Chem. 1965, 30. 3084) indicate that the use of aqueous alcoholic solvent causes the formation of ketones in addition to or instead of oxazolines. These authors stated that the use of anhydrous solvent was required in order to cleanly prepare the desired oxazolines. The procedure described in this paper utilizes N,N-dimethylformamide as solvent in their oxazoline preparations. While the paper of Easton et al. discloses the use of silver nitrate as a catalyst for cyclization, they employed 0.2–0.44 equivalents (20 to 44 mol %) of the "catalyst" and required a reaction time of 3 h. The process of the present invention uses only 0.1–5 mol % of catalyst and the reactions are often complete in <1 h. Furthermore, a wide variety of metal salts and solvents can be employed and water is tolerated without adverse effect in the present invention.

U.S. Pat. Nos. 4,822,902 and 5,304,572 disclose the formation of 5-(chloromethylene)oxazolines which are obtained by treating an alkynyl amide with chlorine. However, the use of TCIA as a chlorinating agent is not disclosed or suggested. These references, either by themselves or taken together, do not suggest the process of the present invention.

One embodiment of this invention provides a convenient process to α-chloroketones, which are useful as fungicides, comprising the steps of cyclizing a substituted alkynyl amide, optionally in the presence of an organic solvent using a catalytic quantity of a metal salt to form a 5-methyleneoxazoline in a first step, chlorinating the 5-methyleneoxazoline in a solvent using trichloroisocyanuric acid to produce a chlorinated oxazoline intermediate in a second step, and subsequently hydrolyzing the chlorinated oxazoline intermediate with an aqueous acid to produce the desired monochloroketone in a third step. The ketone is typically isolated by a crystallization-filtration procedure.

Specifically, this embodiment provides a process for the preparation of an α-chloroketone compound of formula (I) comprising the steps of (i) cyclizing an alkynyl amide of formula (II), optionally in the presence of an organic solvent, using a catalytic quantity of a metal salt to form a 5-methyleneoxazoline of formula (III)

(ii) chlorinating the 5-methyleneoxazoline of formula (III) in a solvent using trichloroisocyanuric acid to produce a chlorinated oxazoline intermediate of formula (IV)

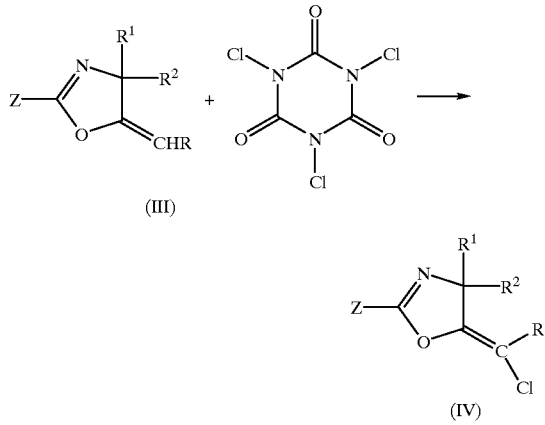

and (iii) hydrolyzing the chlorinated oxazoline intermediate of formula (IV) with an aqueous acid to produce the desired monochloroketone of formula (I)

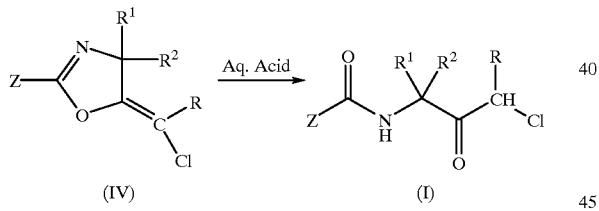

wherein

Z is alkyl or substituted alkyl, aryl or substituted aryl, heteroaryl or substituted heteroaryl or phenylene, R is a hydrogen atom or alkyl, and $R^1$ and $R^2$ are each independently an alkyl or substituted alkyl group, or $R^1$ and $R^2$ together with the carbon atom to which they are attached form a cyclic structure.

In a preferred form of this embodiment,

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro, cyano, 2-naphthyl, 3-pyridyl and 1,4-phenylene, R is a hydrogen atom or a $(C_1-C_4)$alkyl, and $R^1$ and $R^2$ are each independently a $(C_1-C_4)$alkyl or $R^1$ and $R^2$ together with the carbon atom to which they are attached form a cyclopentyl or cyclohexyl ring.

In a more preferred form of this embodiment,

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, R is a hydrogen atom, methyl or ethyl, and $R^1$ and $R^2$ are each independently methyl or ethyl or $R^1$ and $R^2$ together with the carbon atom to which they are attached form a cyclohexyl ring.

In an even more preferred form of this embodiment,

Z is 4-chlorophenyl, 2,6-difluorophenyl, 3,5-dimethylphenyl, 3,5-dichloro-4-methylphenyl, 1,4-phenylene, 2-naphthyl, 3-pyridyl or 3-heptyl, R is a hydrogen atom, and $R^1$ and $R^2$ are each independently methyl or ethyl.

In a second embodiment of this invention, the amount of TCIA which is employed in step (ii) may be advantageously increased in order to form 5-(dichloromethylene)oxazolines which are subsequently hydrolyzed to $\alpha,\alpha$-dichloroketones which are useful as fungicides. Specifically, this feature of this invention provides a process for the preparation of an $\alpha,\alpha$-dichloroketone compound of formula (IA) comprising the steps of (i) cyclizing an alkynyl amide of formula (IIA), optionally in the presence of an organic solvent, using a catalytic quantity of a metal salt to form a 5-methyleneoxazoline of formula (IIIA)

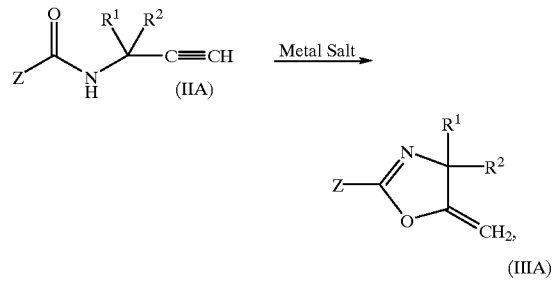

(ii) chlorinating the 5-methyleneoxazoline of formula (IIIA) in a solvent using trichloroisocyanuric acid to produce a dichlorinated oxazoline intermediate of formula (IVA)

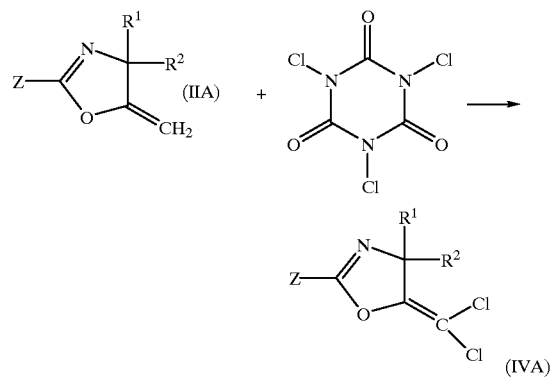

and (iii) hydrolyzing the dichlorinated oxazoline intermediate of formula (IVA) with an aqueous acid to produce the desired dichloroketone of formula (IA)

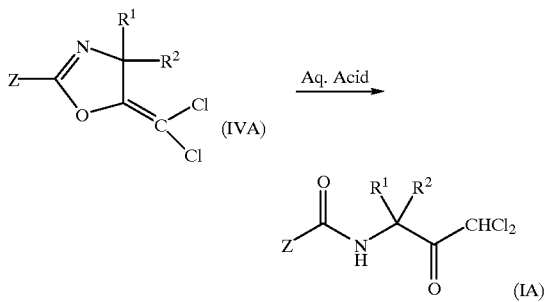

wherein
- Z is alkyl or substituted alkyl, aryl or substituted aryl, heteroaryl or substituted heteroaryl or phenylene, and
- $R^1$ and $R^2$ are each independently an alkyl or substituted alkyl group, or $R^1$ and $R^2$ together with the carbon atom to which they are attached form a cyclic structure.

In a preferred form of this embodiment,
- Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro, cyano, 2-naphthyl, 3-pyridyl and 1,4-phenylene, and
- $R^1$ and $R^2$ are each independently a $(C_1-C_4)$alkyl or $R^1$ and $R^2$ together with the carbon atom to which they are attached form a cyclopentyl or cyclohexyl ring.

In a more preferred form of this embodiment,
- Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl, 3-pyridyl or 1,4-phenylene, and
- $R^1$ and $R^2$ are each independently methyl or ethyl or $R^1$ and $R^2$ together with the carbon atom to which they are attached form a cyclohexyl ring.

In an even more preferred form of this embodiment,
- Z is 4-chlorophenyl, 2,6-difluorophenyl, 3,5-dimethylphenyl, 3,5-dichloro-4-methylphenyl, 1,4-phenylene, 2-naphthyl, 3-pyridyl or 3-heptyl, and
- $R^1$ and $R^2$ are each independently methyl or ethyl.

In this invention, alkyl means a $(C_1-C_8)$ straight or a $(C_3-C_8)$ branched chain alkyl group and includes, for example, methyl, ethyl, n-propyl, isopropyl, n-butyl, isobutyl, sec-butyl, tert-butyl, n-amyl, isoamyl, n-hexyl, isooctyl and the like. Substituted alkyl means an alkyl substituted with one or more substituents selected from the group consisting of alkoxy, halo, alkylthio and cyano.

Alkoxy means a $(C_1-C_4)$ straight or a $(C_3-C_4)$ branched chain alkyl group attached to an oxygen atom, for example, methoxy, ethoxy, isobutoxy and the like.

Alkylthio means a $(C_1-C_4)$ straight or a $(C_3-C_4)$ branched chain alkyl group attached to an sulfur atom, for example, methylthio, n-propylthio, sec-butylthio and the like.

Halo means bromo, chloro, fluoro and iodo.

Aryl means phenyl, naphthyl, or phenyl or naphthyl substituted with one to three substituents independently selected from the group consisting of halo, alkyl, alkynyl, alkoxy, nitro and cyano. Examples include, but are not limited to, phenyl, 2-naphthyl, 4-nitrophenyl, 4-chlorophenyl, 3,5-dimethylphenyl, 2,6-difluorophenyl, 3,5-dichloro-4-methylphenyl, 3,5-dichlorophenyl, 3,5-difluorophenyl, 3,5-dibromophenyl, 3-chloro-4-ethyl-5-fluorophenyl, 3,5-dichloro-4-cyanophenyl, 3,5-dichloro-4-methoxyphenyl, 3,5-difluoro-4-propargylphenyl, 3,5-dibromo-4-methylphenyl and the like.

Alkynyl means a $(C_2-C_6)$alkynyl, for example, ethynyl, propargyl, 2-hexyn-1-yl and the like.

Heteroaryl means a 5-membered aromatic ring which may contain an oxygen atom, a sulfur atom, 1, 2 or 3 nitrogen atoms, an oxygen atom with 1 or 2 nitrogen atoms or a sulfur atom with 1 or 2 nitrogen atoms, or a 6-membered aromatic ring containing 1, 2 or 3 nitrogen atoms, or heteroaryl substituted with up to two substituents selected from halo, alkyl, haloalkyl or cyano. Examples include, but are not limited to 2-furyl, 2-thienyl, 4-chloro-2-thienyl, 2-oxazolyl, 2-imidazolyl, 1,2,4-triazol-1-yl, 2-imidazolyl, 2-pyrrolyl, 2-pyridyl, 3-pyridyl, 4-pyridyl, 4-pyridazinyl, 4-pyrimidinyl, 2-pyrazinyl, 1,3,5-triazin-2-yl, 4-chloro-3-pyridyl and the like.

Phenylene means 1,4-phenylene.

Although a specific isomer is shown throughout for the compound of formula (IV), it is to be understood that formula (IV) actually represents a mixture of the cis and trans isomeric forms.

In the first embodiment of this invention, the cyclization step (i) to form a 5-methyleneoxazoline from an alkynyl amide is carried out using a catalytic amount of a metal salt, optionally in the presence of an organic solvent. A solvent is usually employed since the amide starting materials are solids. Preferred solvents are those with suitable boiling points, from about 75° C. to about 150° C., for ease of removal after the reaction. More preferred are those solvents with a boiling point from about 90° C. to about 150° C. Preferred solvents include, but are not limited to, aliphatic hydrocarbons such as isooctane, aromatic hydrocarbons such as toluene and xylenes, ketones such as methyl isobutyl ketone, esters such as butyl acetate, halohydrocarbons such as chlorobenzene, and nitrites such as isobutyronitrile.

Various metal catalysts are used for the cyclization of the alkynyl amide to the 5-methyleneoxazoline. Catalysts that are useful include salts of copper, silver, palladium, zinc, iron, manganese, nickel, cerium, cobalt, platinum, rhodium and ruthenium. Examples include, but are not limited to, copper(I) chloride, copper(I) oxide, silver nitrate, palladium (II) acetate, zinc chloride, iron(III) oxide, iron(II) acetate, manganese(II) sulfate, nickel oxide, nickel chloride, nickel acetate tetrahydrate, cerium(III) carbonate, cobalt(II) acetate, platinum(II) chloride, rhodium(III) chloride, and ruthenium(III) chloride. Preferred metal salts because of the resulting reaction kinetics and/or reaction selectivity are those of copper, silver, palladium, zinc and ruthenium. Even more preferred metal salts are those of copper, silver and zinc. Solid supported reagents such as silver-exchanged zeolite may also be employed. The amount of catalyst usually employed is from about 0.1 mol % to about 5 mol % based on the alkynyl amide. A preferred amount of catalyst is <5 mol %, a more preferred amount is <2 mol % and an even more preferred amount is <1 mol %.

The reaction temperature is usually about 60° C. up to the boiling point of the solvent used. A preferred condition is a reaction temperature of at least 70° C. up to the boiling point of the solvent used. However, the reaction may be conveniently run at a temperature as low as about 35° C. when silver nitrate is employed as the catalyst. Pressure is not important, but the reaction is usually run at atmospheric pressure for convenience. The time of the reaction will depend upon the temperature employed, the substituent pattern of the starting alkynyl amide, the solvent utilized, the nature of the metal catalyst, and the size and design of the reactor. However, the reaction is usually conveniently effected in a time of 18 hours or less and more usually 7 hours or less.

In a typical representative reaction procedure for step (i), the alkynyl amide was combined with the solvent, if employed, and the metal salt catalyst, and the resulting mixture then heated to the desired temperature. The reaction was monitored by gas chromatography. When the cyclization to the oxazoline was judged to be complete, the reaction was cooled to room temperature and washed with water or, in the case of copper salts, hydrochloric acid followed by water. For palladium salts, the reaction mixture was passed through a pad of silica gel. The organic layer was in some cases dried over sodium sulfate and filtered. The solvent was removed by evaporation under reduced pressure, and the residue was dried in a vacuum oven to afford the oxazoline product. The crude oxazoline products can be utilized directly for further reactions or, if desired, can be purified by distillation. Alternatively, the reaction mixture can be taken on to the chlorination step without any workup since the salts present are removed on washing after cyanuric acid filtration following the chlorination.

The chlorination step (ii) of the 5-methyleneoxazoline using TCIA may be performed at a temperature of from about −30° to about 100° C. A preferred chlorination temperature is from about 0° to 70° C. More preferred is a temperature of about 50° C. or lower. Even more preferred is a temperature from 0° to 30° C. The reaction is not pressure-dependent, but a pressure of 1 atmosphere is usually preferred for convenience. The stoichiometry of the reagents is extremely important. If less than 0.333 equivalent of TCIA per equivalent of 5-methyleneoxazoline is used, some of the 5-methyleneoxazoline starting material will remain unreacted. If greater than 0.333 equivalent is used, an overchlorinated intermediate is formed that leads to a dichloroketone after hydrolysis. However, as noted previously, a second embodiment of this invention provides for the convenient formation of either the 5-(dichloromethylene)oxazoline or the 5-chloro-5-(dichloromethylene)oxazoline intermediate and subsequent formation in step (iii) of an α,α-dichloroketone when ≧0.667 equivalent of TCIA is used per equivalent of the 5-methyleneoxazoline in the situation where the methylene group of the 5 oxazoline is not substituted with an alkyl group. The chlorination reaction time can vary from about 5 minutes to about 1 hour and is dependent on both the size and type of reactor equipment employed and the solvent used. The chlorination solvent is usually a polar solvent such as, but not limited to, an ether, an ester or a ketone, for example ethyl acetate, butyl acetate, methyl isobutyl ketone and methyl t-butyl ether. Preferred solvents are ethyl acetate, butyl acetate and methyl isobutyl ketone. Nonpolar solvents such as an aromatic hydrocarbon, for example toluene, or an aliphatic hydrocarbon, for example heptane and isooctane, may be also employed when admixed with a miscible polar type solvent or when heated to a temperature of about 40° C. After the chlorination reaction is carried out to the desired stage, the cyanuric acid by-product may be removed by filtration and/or by washing with a common base such as sodium carbonate, sodium hydroxide and the like. The resulting solution containing the 5-(chloromethylene) oxazoline is then subjected to the hydrolysis step (iii).

In the hydrolysis step (iii), a temperature of about 50° C. or higher is required. Preferably, the hydrolysis is performed from about 50° to 100° C. More preferably, the temperature employed is from about 50° to 80° C. Either an aqueous acid or a non-aqueous acid admixed with some water may be employed. A common acid such as, but not limited to, hydrochloric acid, sulfuric acid, trifluoroacetic acid, methanesulfonic acid or toluenesulfonic acid is convenient to use. Aqueous hydrochloric acid or sulfuric acid are preferred. An acidic ion-exchange resin may also be utilized. When hydrochloric acid or sulfuric acid is used, additional water is usually added to facilitate the hydrolysis. It is preferred that about 0.05 to 0.5 equivalent of an aqueous acid is used per equivalent of 5-(chloromethylene)oxazoline. More preferred is the use of about 0.1 to 0.25 equivalent of aqueous hydrochloric acid per equivalent of 5-(chloromethylene) oxazoline. The hydrolysis step usually takes from about 3 to about 24 hours, with the time depending on the nature of the group, the temperature and the size and nature of the equipment employed. The pressure used is not critical. However, 1 atmosphere is usually preferred for convenience.

In a typical representative reaction procedure for steps (ii) and (iii), the oxazoline and solvent are combined and the resulting solution is chilled to 0–5° C. using an ice bath. The TCIA is added gradually, keeping the reaction temperature below 30° C. if possible. Once the TCIA has been added, the resulting slurry is warmed to room temperature and stirred until the reaction is complete based on gas chromatographic (GC) analysis. The cyanuric acid by-product is removed by filtration and the solution is then washed with an appropriate base such as a sodium bicarbonate or sodium hydroxide solution to remove any remaining cyanuric acid. The solution containing the 5-(chloromethylene)oxazoline is returned to the flask and heated to 60–80° C. Concentrated hydrochloric acid and water are added and the solution is stirred until the hydrolysis is complete. The reaction mixture is cooled to room temperature and the desired α-chloroketone crystallizes on cooling. The solid obtained is filtered, washed and dried to give the product. A second crop is frequently obtained by concentration and cooling of the filtrate solution.

The following examples, tables and experimental procedures are provided for guidance to the practitioner and are not meant to limit the scope of the invention which is defined by the claims.

EXAMPLE M1

Preparation of 4,4-dimethyl-5-methylene-2-phenyloxazoline

A round bottom flask was charged with N-(3-methylbutyn-3-yl)benzamide (5.0 g, 26.7 mmol), silver nitrate (9.1 mg, 0.2 mol %), and n-butyl acetate (20 mL). The resulting mixture was heated to 95° C. for 0.5 h, then cooled to room temperature. The reaction was washed with water, and the organic layer was dried over anhydrous sodium sulfate. The solvent was removed by evaporation under reduced pressure. The residue was dried in a vacuum oven to give 4,4-dimethyl-5-methylene-2-phenyloxazoline (4.67 g 93% yield) as a pale yellow oil (bp 70–75° C., 0.6 mm Hg).

EXAMPLE M3

Preparation of 2-(4-chlorophenyl)-4,4-dimethyl-5-methyleneoxazoline

A round bottom flask was charged with N-(3-methylbutyn-3-yl)-4-chlorobenzamide (4.5 g, 19.09 mmol), copper(I) chloride (9.5 mg, 0.5 mol %), and n-butyl acetate (20 mL). The resulting mixture was heated to 95° C. for 4 h, then cooled to room temperature. The reaction was washed with 1 M hydrochloric acid solution and with water. The organic layer was dried over anhydrous sodium sulfate. The solvent was removed by evaporation under reduced pressure, and the residue was dried in a vacuum oven to afford 2-(4-chlorophenyl)-4,4-dimethyl-5-methyleneoxazoline (4.24 g, 94% yield) as a pale yellow oil (bp 95° C., 0.6 mm Hg).

Following the general procedures of examples M1 and M3, the oxazolines of examples M2 and M4–M10 were prepared using the appropriate alkynyl amide, metal salt catalyst, solvent, reaction temperature and time as shown in Table I.

flask was chilled in a refrigerator at 8° C. overnight. The resulting slurry was filtered to obtain a second crop of crystals. Both crops were dried at 60° C. under vacuum, yielding N-(1-chloro-3-methyl-2-oxopent-3-yl)-3,5-dichloro-4-methylbenzamide (10.31 g, 87%) as a white solid, (mp 157–1,58° C.).

By following substantially the same procedure, the compounds of Examples $C_1$–$C_5$ and $C_7$–$C_9$ were prepared as shown in Table II.

TABLE I

EXAMPLES M1 to M10
Metal Salt Catalyzed Formation of 5-Methyleneoxazolines from Alkynyl Amides

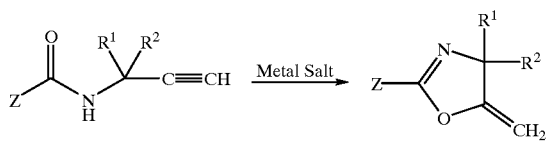

| Example No. | Z | $R^1$ | $R^2$ | Catalyst, Amount | Solvent, Temperature | Time (h) | % Yield | bp ° C., (mm Hg) |
|---|---|---|---|---|---|---|---|---|
| M1 | phenyl | $CH_3$ | $CH_3$ | $AgNO_3$ 0.2 mol % | n-butyl acetate 95° C. | 0.5 | 93 | 70–75° (0.6) |
| M2 | 3,5-dimethylphenyl | $CH_3$ | $CH_3$ | CuCl 5 mol % | n-butyl acetate 90° C. | >1 | 87 | 86–94° (0.4) |
| M3 | 4-chlorophenyl | $CH_3$ | $CH_3$ | CuCl 0.5 mol % | n-butyl acetate 90° C. | 4 | 94 | 95° (0.6) |
| M4 | 2,6-difluorophenyl | $CH_3$ | $CH_3$ | $Pd(OAc)_2$ 1 mol % | methyl isobutyl ketone, 100° C. | 7 | 100 | 80° (1.0) |
| M5 | 2,6-difluorophenyl | —$(CH_2)_5$— | | $ZnCl_2$ 0.5 mol % | isobutyronitrile 95° C. | 7 | 92 | 110–112° (0.5) |
| M6 | 3,5-dichloro-4-methylphenyl | $CH_3$ | $CH_2CH_3$ | $AgNO_3$ 0.05 mol % | n-butyl acetate ($H_2O$-saturated) 35–40° C. | 1 | 97 | 128° (1.0) |
| M7 | 3,5-dichloro-4-methylphenyl | $CH_3$ | $CH_2CH_3$ | $RuCl_3 \cdot 3\,H_2O$ 5 mol % | n-butyl acetate 90° C. | <12 | 90 | 128° (1.0) |
| M8 | 1,4-phenylene | $CH_2CH_3$ | $CH_2CH_3$ | $ZnCl_2$ 0.5 mol % | n-butyl acetate 100–110° C. | <18 | 99 | mp 143–144° |
| M9 | 2-naphthyl | $CH_3$ | $CH_3$ | $Pd(OAc)_2$ 0.5 mol % | toluene 95° C. | 0.5 | 100 | 132–137° (0.5) |
| M10 | heptan-3-yl | $CH_3$ | $CH_3$ | $AgNO_3$ 0.2 mol % | toluene 75° C. | 0.5 | 87 | 62° (1.0) |

EXAMPLE C6

Preparation of N-(1-chloro-3-methyl-2-oxopent-3-yl)-3,5-dichloro-4-methylbenzamide A solution of 2-(3,5-dichloro-4-methylphenyl)-4-ethyl-4-methyl-,5-methyleneoxazoline (10.0 g, 35.19 mmol) and ethyl acetate (25 mL) was cooled to 5° C. using an ice bath. Trichloroisocyanuric acid (2.73 g, 11.73 mmol) was added in several portions over 15 minutes in order to keep the reaction temperature below 40° C. When the addition was complete the reaction mixture was cooled to 20° C., and the ice bath was removed. The reaction was monitored by GC analysis for disappearance of the starting material and was judged to be complete after 1 h. The mixture was filtered; the wetcake was washed with ethyl acetate (5 mL). The filtrate was transferred to a round-bottom flask and heated to 60° C. Hydrochloric acid (0.69 g of a 37% solution) and water (2.2 mL) were added. The reaction mixture was stirred at 60° C. for 1.5 h, then at 73° C. for an additional 1.5 h. The reaction was then cooled to room temperature. The resulting slurry was stored in a refrigerator overnight. The mixture was filtered, and the solids were rinsed with cold filtrate solution. The filtrate was concentrated to approximately half of its original volume by evaporation under reduced pressure. A seed crystal of product from the first crop was added, and the

TABLE II

Preparation of α-Chloroketones from a
5-Methyleneoxazoline and TCIA, Followed by Hydrolysis

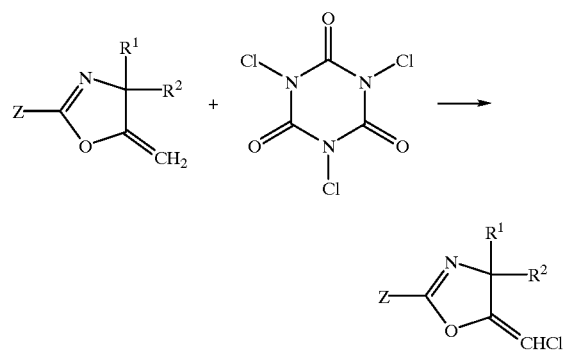

TABLE II-continued

Preparation of α-Chloroketones from a
5-Methyleneoxazoline and TCIA, Followed by Hydrolysis

| Example No. C | Z | R¹ | R² | Product Yield (%) | mp (°C.) |
|---|---|---|---|---|---|
| 1 | phenyl | $CH_3$ | $CH_3$ | 74 | 154–155 |
| 2 | 3,5-dimethylphenyl | $CH_3$ | $CH_3$ | 75 | 162–164 |
| 3 | 4-chlorophenyl | $CH_3$ | $CH_2CH_3$ | 76 | 113–114 |
| 4 | 2,6-difluorophenyl | $CH_3$ | $CH_3$ | 75 | 191–192 |
| 5 | 2,6-difluorophenyl | —$(CH_2)_5$— | | 74 | 171–172 |
| 6 | 3,5-dichloro-4-methylphenyl | $CH_3$ | $CH_2CH_3$ | 87 | 157–158 |
| 7 | 1,4-phenylene | $CH_2CH_3$ | $CH_2CH_3$ | 60 | 193–196 |
| 8 | 2-naphthyl | $CH_3$ | $CH_3$ | 60 | 151–152 |
| 9 | heptan-3-yl | $CH_3$ | $CH_3$ | 58 | 58–60 |

To further illustrate the benefits of the present invention by using TCIA as a chlorinating agent for 5-methyleneoxazolines, the following comparative examples were performed with other conventional chlorinating agents.

COMPARATIVE EXAMPLE C-1
Use of Chlorine Gas

A solution of 2-(3,5-dichloro-4-methylphenyl)-4-ethyl-4-methyl-5-methyleneoxazoline (20.0 g, 70.4 mmol) and methanol (100 mL) was cooled to 0° C. Chlorine gas was bubbled into the solution; the reaction was monitored by gas chromatography.[1] The chlorine feed was halted when the starting material disappeared (1.5 h). The solution was purged with nitrogen to remove any remaining chlorine, then the solution was heated to 50° C. Water (20 mL) was added, and the reaction was stirred until hydrolysis was complete. The reaction mixture was cooled to room temperature, and the slurry was filtered. The wetcake was washed with cold solution of 10% water in methanol and dried in a vacuum oven to yield 15.89 g of white solid. The product contained 71% N-(1-chloro-3-methyl-2-oxopent-3-yl)-3,5-dichloro-4-methylbenzamide, 16% N-(1,1-dichloro-3-methyl-2-oxopent-3-yl)-3,5-dichloro-4-methylbenzamide, and 0.8% N-(3-methyl-2-oxopent-3-yl)-3,5-dichloro-4-methylbenzamide. The yield of the desired monochloroketone was estimated at 48%. (Compare to Example C6).

[1] NOTE WELL: Mixtures of chlorine gas and methanol can form methyl hypochlorite which is explosive and shock-sensitive.

COMPARATIVE EXAMPLE C-2
Use of N-Chlorosuccinimide

A solution of 2-(3,5-dichloro-4-methylphenyl)-4-ethyl-4-methyl-5-methyleneoxazoline (5.0 g, 17.6 mmol) and ethyl acetate (20 mL) was treated with N-chlorosuccinimide (2.3.5 g, 17.6 mmol). The solution was stirred at ambient temperature for 70 h. The reaction mixture contained 50% unreacted starting material and 50% of the desired 5-chloromethylene-2-(3,5-dichloro-4-methylphenyl)-4-ethyl-4-methyloxazoline. (Compare to Example C6).

It is to be understood that changes and variations in this invention may be made without departing from the spirit and scope of this invention as defined by the appended claims.

I claim:

1. A process for the preparation of an α-chloroketone compound of formula (I) comprising the steps of (i) cyclizing an alkynyl amide of formula (II), optionally in the presence of an organic solvent, using a catalytic quantity of a metal salt to form a 5-methyleneoxazoline of formula (III)

(ii) chlorinating the 5-methyleneoxazoline of formula (III) in a solvent using trichloroisocyanuric acid to produce a chlorinated oxazoline intermediate of formula (IV)

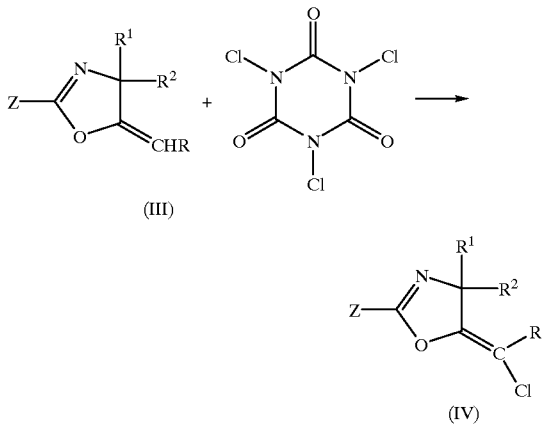

and (iii) hydrolyzing the chlorinated oxazoline intermediate of formula (IV) with an aqueous acid to produce the desired monochloroketone of formula (I)

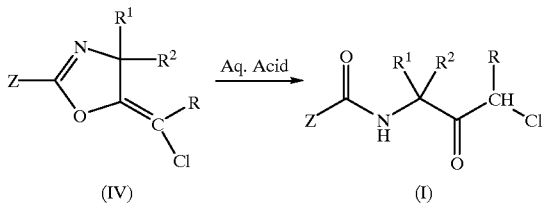

wherein

Z is alkyl or substituted alkyl, aryl or substituted aryl, heteroaryl or substituted heteroaryl, R is a hydrogen atom or alkyl, and $R^1$ and $R^2$ are each independently an alkyl or substituted alkyl group, or $R^1$ and $R^2$ together with the carbon atom to which they are attached form a cyclic structure.

2. The process of claim 1 wherein

Z is ($C_1$–$C_8$)alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro, cyano, 2-naphthyl and 3-pyridyl, R is a hydrogen atom or a $(C_1-C_4)$alkyl, and $R^1$ and $R^2$ are each independently a $(C_1-C_4)$alkyl or $R^1$ and $R^2$ together with the carbon atom to which they are attached form a cyclopentyl or cyclohexyl ring.

3. The process of claim 2 wherein

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 2-naphthyl, 3-pyridyl or 4-nitrophenyl, R is a hydrogen atom, methyl or ethyl, and $R^1$ and $R^2$ are each independently methyl or ethyl or $R^1$ and $R^2$ together with the carbon atom to which they are attached form a cyclohexyl ring.

4. The process of claim 3 wherein

Z is 4-chlorophenyl, 2,6-difluorophenyl, 3,5-dimethylphenyl, 3,5-dichloro-4-methylphenyl, 2-naphthyl, 3-pyridyl or 3-heptyl, R is a hydrogen atom, and $R^1$ and $R^2$ are each independently methyl or ethyl.

5. The process of claim 1 wherein the metal salt catalyt used in step (i) is a salt of copper, silver, palladium, zinc, iron, manganese, nickel, cerium, cobalt, platinum, rhodium or ruthenium.

6. The process of claim 5 wherein the metal salt catalyt is a salt of copper, silver, palladium, zinc or ruthenium.

7. The process of claim 5 wherein the metal salt catalyst is a solid supported reagent.

8. The process of claim 5 wherein the amount of catalyst employed is from about 0.1 mol % to about 5 mol % based on the alkynyl amide.

9. The process of claim 1 wherein an organic solvent is employed in step (i).

10. The process of claim 9 wherein the solvent used is an aliphatic hydrocarbons, an aromatic hydrocarbon, a ketone, an ester, a halohydrocarbon or a nitrile.

11. The process of claim 1 wherein the chlorination step (ii) of the 5-methyleneoxazoline is performed at a temperature from −30° to 100° C.

12. The process of claim 1 wherein the solvent of the chlorination step (ii) is a polar solvent, an admixture of a miscible polar and a non-polar solvent, or a mixture of a polar and a non-polar solvent.

13. The process of claim 12 wherein the polar solvent is an ether, in ester or a ketone and the non-polar solvent is an aromatic hydrocarbon or an aliphatic hydrocarbon.

14. A process for the preparation of an α,α-dichloroketone compound of formula (IA) comprising the steps of (i) cyclizing an alkynyl amide of formula (IIA), optionally in the presence of an organic solvent, using a catalytic quantity of a metal salt to form a 5-methyleneoxazoline of formula (IIIA)

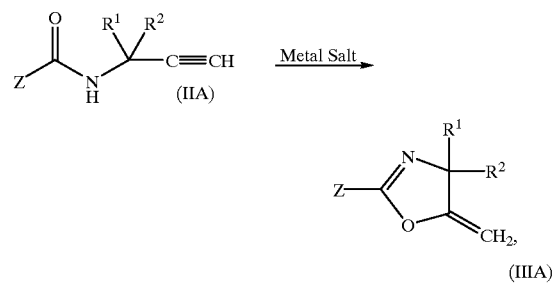

(ii) chlorinating the 5-methyleneoxazoline of formula (IIIA) in a solvent using trichloroisocyanuric acid to produce a dichlorinated oxazoline intermediate of formula (IVA)

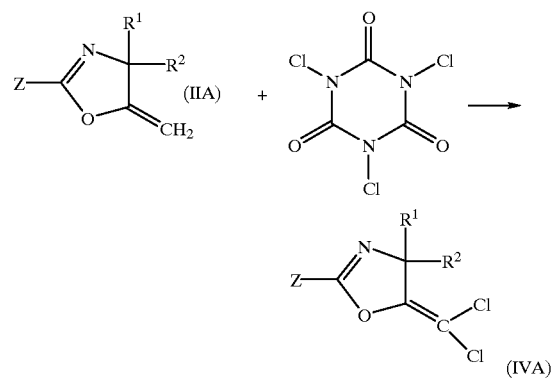

and (iii) hydrolyzing the dichlorinated oxazoline intermediate of formula (IVA) with an aqueous acid to produce the desired α,α-dichloroketone of formula (IA)

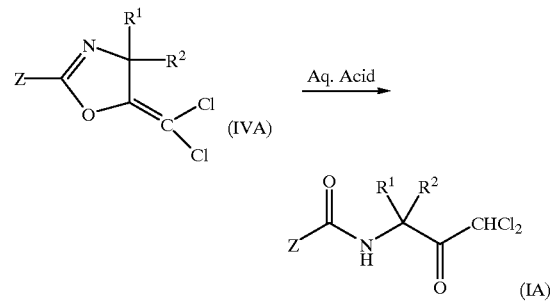

wherein

Z is alkyl or substituted alkyl, aryl or substituted aryl, heteroaryl or substituted heteroaryl, and $R^1$ and $R^2$ are each independently an alkyl or substituted alkyl group, or $R^1$ and $R^2$ together with the carbon atom to which they are attached form a cyclic structure.

15. The process of claim 14 wherein

Z is $(C_1-C_8)$alkyl, phenyl or phenyl substituted with up to three substituents independently selected from the group consisting of halo, $(C_1-C_4)$alkyl, $(C_1-C_4)$alkoxy, $(C_2-C_6)$alkynyl, nitro, cyano, 2-naphthyl and 3-pyridyl, and $R^1$ and $R^2$ are each independently a $(C_1-C_4)$alkyl or $R^1$ and $R^2$ together with the carbon atom to which they are attached form a cyclopentyl or cyclohexyl ring.

16. The process of claim 15 wherein

Z is 3-heptyl, phenyl, 4-halophenyl, 2,6-dihalophenyl, 4-$(C_1-C_4)$alkylphenyl, 3,5-dihalophenyl, 3,5-di$(C_1-C_4)$alkylphenyl, 4-$(C_1-C_4)$alkyl-3,5-dihalophenyl, 4-cyano-3,5-dihalophenyl, 4-$(C_1-C_4)$alkoxy-3,5-dihalophenyl, 4-nitrophenyl, 2-naphthyl or 3-pyridyl, and $R^1$ and $R^2$ are each independently methyl or ethyl or $R^1$ and $R^2$ together with the carbon atom to which they are attached form a cyclohexyl ring.

* * * * *